United States Patent
Neumeyer

(10) Patent No.: US 9,339,358 B2
(45) Date of Patent: May 17, 2016

(54) MEDICAL MEMBRANE, IN PARTICULAR DENTAL MEMBRANE AND TOOTH IMPLANT WITH SUCH A MEMBRANE

(71) Applicant: Stefan Neumeyer, Eschlkam (DE)

(72) Inventor: Stefan Neumeyer, Eschlkam (DE)

( * ) Notice: Subject to any disclaimer, the term of this patent is extended or adjusted under 35 U.S.C. 154(b) by 0 days.

(21) Appl. No.: 13/741,695

(22) Filed: Jan. 15, 2013

(65) Prior Publication Data
US 2013/0189645 A1    Jul. 25, 2013

(51) Int. Cl.
*A61C 8/00* (2006.01)
*A61C 19/06* (2006.01)
*A61C 8/02* (2006.01)
*A61L 27/12* (2006.01)
*A61L 27/38* (2006.01)
*A61L 27/42* (2006.01)
*A61L 27/46* (2006.01)

(52) U.S. Cl.
CPC . *A61C 19/06* (2013.01); *A61C 8/00* (2013.01); *A61C 8/0006* (2013.01); *A61C 8/0013* (2013.01); *A61L 27/12* (2013.01); *A61L 27/3821* (2013.01); *A61L 27/425* (2013.01); *A61L 27/46* (2013.01); *A61L 2430/02* (2013.01); *A61L 2430/12* (2013.01)

(58) Field of Classification Search
USPC ......... 433/172–176; 623/16.11, 17.17, 11.11, 623/1.11, 1.12, 2.11–2.19
See application file for complete search history.

(56) References Cited

U.S. PATENT DOCUMENTS

| | | | | |
|---|---|---|---|---|
| 5,380,328 | A * | 1/1995 | Morgan | 606/70 |
| 5,944,524 | A * | 8/1999 | Hill et al. | 433/173 |
| 6,299,448 | B1 * | 10/2001 | Zdrahala | A61C 8/0006 433/173 |
| 2008/0051866 | A1* | 2/2008 | Chen | A61F 2/91 623/1.11 |
| 2012/0078353 | A1* | 3/2012 | Quadri et al. | 623/2.11 |
| 2012/0277844 | A1* | 11/2012 | Wu | A61F 2/915 623/1.11 |
| 2014/0193776 | A1* | 7/2014 | Thurner | A61L 27/56 433/201.1 |

FOREIGN PATENT DOCUMENTS

DE    10 2010 023 794    10/2011

* cited by examiner

*Primary Examiner* — Yogesh Patel
(74) *Attorney, Agent, or Firm* — Welsh Flaxman & Gitler LLC

(57) ABSTRACT

A medical membrane, in particular a dental membrane for regeneration and/or inducing of tissue, in particular of periodontal tissue and for use in direct contact with bone tissue or connective tissue along with a tooth implant.

4 Claims, 3 Drawing Sheets

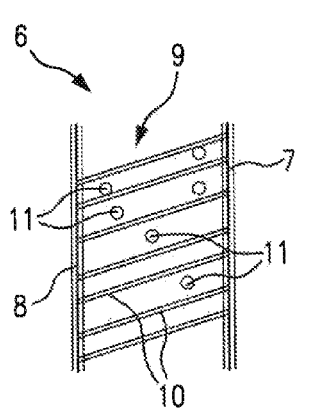
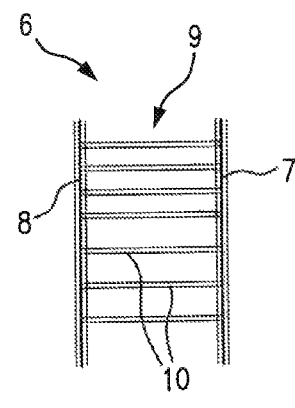
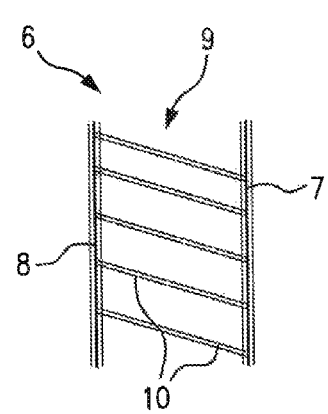
FIG. 3          FIG. 4          FIG. 5
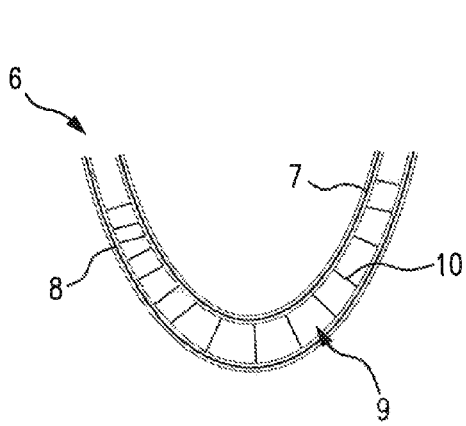
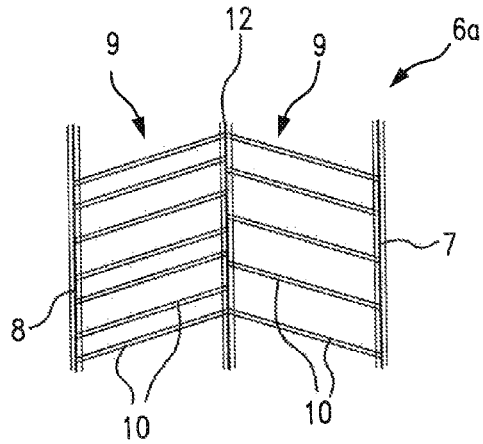
FIG. 6          FIG. 7

MEDICAL MEMBRANE, IN PARTICULAR DENTAL MEMBRANE AND TOOTH IMPLANT WITH SUCH A MEMBRANE

BACKGROUND OF THE INVENTION

1. Field of the Invention

The present invention relates to a medical substrate in the form of a dental membrane for regeneration and/or inducing of tissue, in particular, periodontal tissue, and for use in direct contact with bone tissue or connective tissue. In addition, there is provided a tooth implant incorporating the dental membrane.

2. Description of the Related Art

In dental medicine it is often necessary to restore tissue by regeneration, induction or apposition, in particular but not exclusively alveolar or supra-alveolar tissue, for optimal integration of dental or tooth implants.

Accordingly, it is an object of the invention to present a membrane that enables improved regeneration and improved induction of bone and connective tissue and therefore also improved integration of tooth implants.

SUMMARY OF THE INVENTION

The present invention provides a dental membrane for regeneration and/or inducing of tissue, in particular periodontal tissue. The dental membrane is adapted for use in direct contact with bone tissue or connective tissue, wherein the membrane is composed of at least two layers, preferably, exterior inner and outer layers with at least a central structure positioned therebetween. At least one of the exterior layers is provided, at least to a partial extent, with endogenous bone cells and/or desmodontal cells, structures and/or cell information, and the central structure includes a plurality of fibers.

The term "essentially" or "approximately" as used herein means deviations from the exact value by +/−10%, preferably by +/−5% and/or deviations in the form of changes that are insignificant for the function.

Further embodiments, advantages and possible applications of the invention are disclosed by the following description of exemplary embodiments and the drawings. All characteristics described and/or pictorially represented, alone or in any combination, are subject matter of the invention, regardless of their being summarized or referenced in the claims. The content of the claims is also included as part of the description.

BRIEF DESCRIPTION OF THE DRAWINGS

The invention is described in more detail below based on an exemplary embodiment with reference to the drawings, in which:

FIGS. 3-7 shows schematic representations respectively in cross section of different details of the membrane of FIGS. 1 and 2.

DETAILED DESCRIPTION OF THE INVENTION

Figure 1:
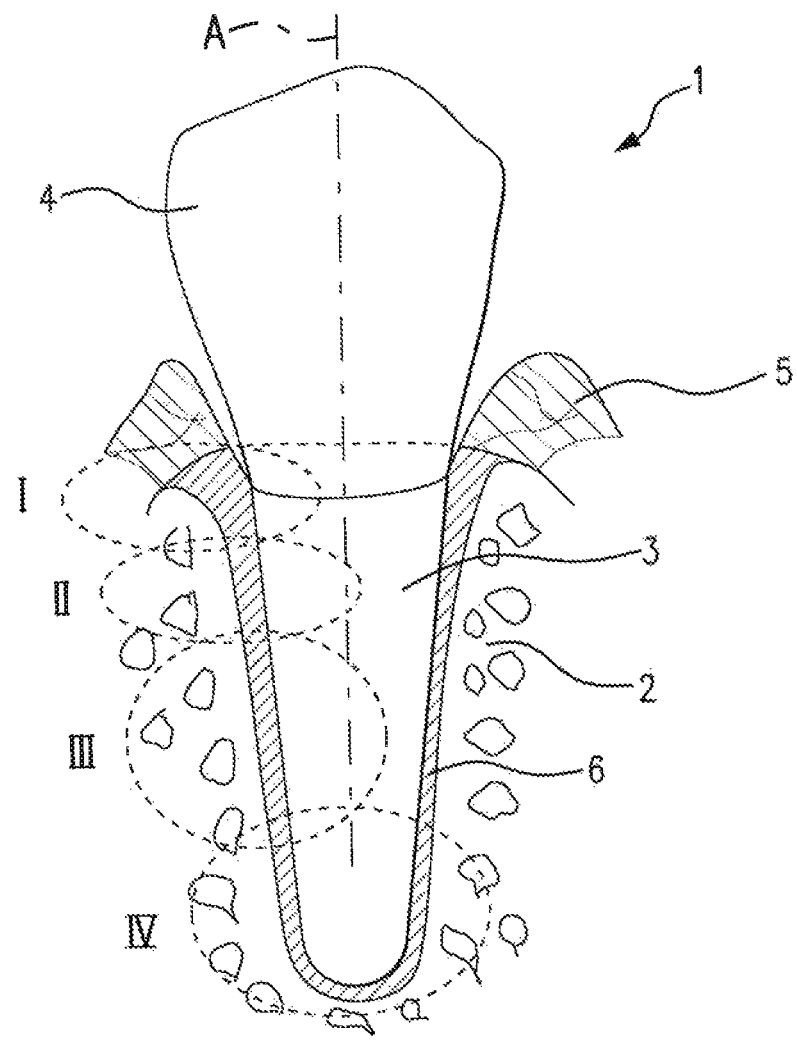
FIG. 1 shows a simplified representation of a tooth implant anchored in an alveolus in the jawbone, with a membrane enclosing the tooth implant at least on a partial length between the implant corpus and an adjoining bone and/or connective tissue.
Figure 2:
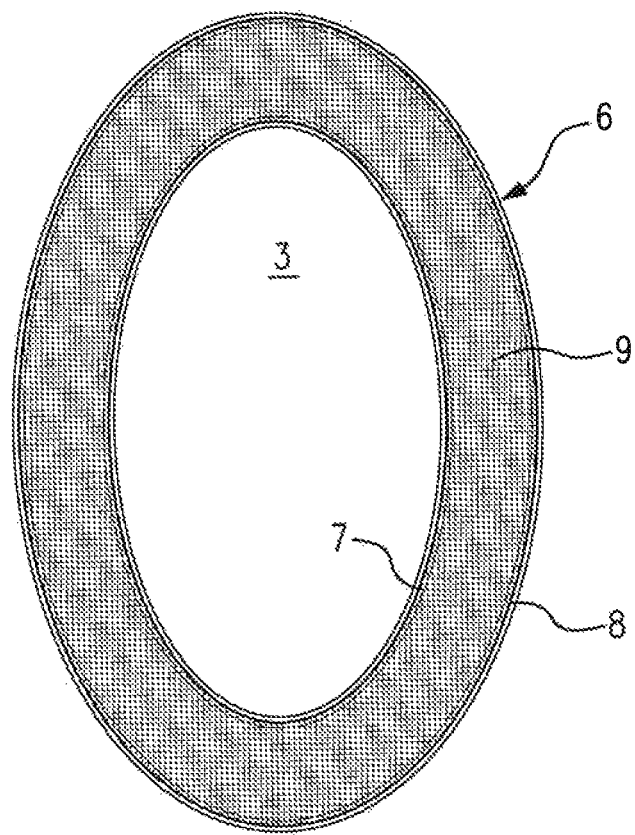
FIG. 2 shows a simplified representation of a cross section through the implant corpus and the membrane enclosing the corpus.

In the drawings, there is depicted a tooth implant 1, which is composed of an implant corpus 3, which is fixed in a jaw bone, or in the bone tissue, 2. The implant corpus 3 is preferably made of a metal material and/or a ceramic. The tooth implant 1 also includes a cap 4 adapted to the natural form of the replaced tooth. The cap 4 is composed of a suitable material for this purpose, for example, a ceramic.

At least on a partial length of the implant corpus 3, a membrane 6 is provided between the implant corpus 3 and the bone tissue 2 or a connective tissue 5, as shown in FIG. 1. The membrane 6 encloses in the manner of a sleeve the implant corpus 3 and, if applicable, also the cap 4 on the coronal area of the implant corpus 3, for promoting healing of the tooth implant 1 and/or for improving the integration or assimilation of the tooth implant 1 into the bone tissue 2 and/or the connective tissue 5.

Referring to FIGS. 3-6 the membrane 6 comprises at least three different structures or layers, which are arranged concentrically, or essentially concentrically, to an axis that corresponds to axis A of the longitudinal extension of the implant corpus 3. The membrane 6 comprises at least an inner layer 7 on the implant side, an outer layer 8 on the tissue side and a central structure 9 in between. These inner layer 7, the outer layer 8 and the central structure 9 are preferably embodied in a porous or lattice-like three-dimensional carrier substrate that is not depicted. The Inner layer 7, the outer layer 8 and/or the central structure 9 is preferably provided at least to a partial extent with endogenous or the patient's own bone cells and/or with endogenous or the patient's own desmodontal cells or structures and/or information. The central structure 9 is fibrous and embodied to simulate the natural fiber apparatus or tooth holding apparatus, based on the position of the membrane 6 on the tooth implant 1 or implant corpus 3.

If the membrane 6 is provided in the coronal area of the implant corpus 3 and thereby at the transition to the cap 4 (see position designated I in FIG. 1), then the central structure 9 is composed of fibers 10 that are oriented at an angle to axis A from the inner layer 7 nearer or adjacent to the implant corpus 3, namely apical, i.e. the fibers 10, with their longitudinal extension, enclose an angle with the axis A which (angle) opens toward the lower apical end of the implant corpus 3. Also, in addition to these fibers 10, the central structure 9 comprises intercircular fibers 11 relative to axis A, i.e. fibers 11 enclosing the tooth implant 1 and/or the axis A, simulating the natural supra-alveolar fiber apparatus or ligament for improved integration of the tooth implant 1 in the gums or connective tissue 5, as shown in FIG. 3.

If the membrane 6 is, at the position designated II in FIG. 1, at a distance beneath the coronal area of the implant corpus 3, but at a larger distance from the apical end of the implant corpus 3, then the fibers 10 of the central structure 9 are oriented radially or essentially radially to axis A, as shown in FIG. 4.

If the membrane 6 is located at the area of the implant corpus 3 designated III in FIG. 1, i.e. in further proximity of the apical end of the implant corpus 3, then the fibers 10 of the central structure 9 are oriented radially but at an angle to axis A corresponding to FIG. 5, so that they enclose with this axis an angle smaller than 90°, which opens toward the coronal end of the implant corpus 3.

If the membrane 6 is located at the area designated IV in FIG. 1, i.e. at the apical end of the implant corpus 3, then the fibers 10 forming the central structure 9 are arranged corresponding to FIG. 6 so that they are oriented with their respective longitudinal extension perpendicular, or essentially perpendicular, to the surface of the apical end and in the depicted embodiment, the rounded end of the implant corpus 3 or to the inner layer 7 enclosing the end.

Preferably the central structure 9 also comprises, on at least one of areas II-IV, additional fibers, in addition to the fibers 10, for example, intercircular fibers 11 crossing the fibers 10 and/or the axis A and the implant corpus 3.

In accordance with an alternate embodiment as shown in FIG. 7, the membrane 6a comprises adjacent central structures 9. Such structure is especially suitable for use in the coronal or in the supra-alveolar area of the tooth implant 1, for improving the connection of the connective tissue 5 to the tooth implant 1 and/or for promoting the integration of the tooth implant 1 in the connective tissue 5 or gums.

The membrane 6a comprises the two adjacent central structures 9, which are preferably structured in a manner similar to the central structure described above. Between the two central structures 9, an additional median structure 12 is provided, from which the fibers 10 of the two central structures 9 start. In the embodiment depicted in FIG. 7, the fibers 10 of the two central structures 9 are oriented at an angle to the median structure 12. The orientation of the fibers 10 in both central structures 9 can be the same or, as shown in FIG. 7, the orientation of the fibers 10 in the central structures 9 can be different, or such that the fibers 10 in both central structures 9 enclose with the median structure 12 an angle smaller than 90° and this angle opens toward a common side, for example, the apical or coronal end. Other orientations of the fibers 10 are also possible, preferably adapted to the position of the membrane 6a on the implant corpus 3.

It has been shown that in the case of the tooth implant 1 (which as opposed to a corresponding natural tooth is anchored firmly or essentially firmly, i.e. not elastically, in the jaw bone) the integration of the tooth implant 1, especially in the connective tissue, is improved significantly, if between the inner layer 7, which is firmly connected in a suitable manner with the tooth implant 1 or with the implant corpus 3 (for example, by adhesion or by natural growth) and the outer layer 8 integrated in the natural tissue (bone tissue 2, connective tissue 5, etc.) the central structure 9 and median structure 12 are positioned. Due to the flexibility of the median structure 12 resulting from the fibers 10, the corresponding properties of the natural supra-alveolar area of the tooth holding apparatus are optimally simulated, so that optimal integration of the tooth implant 1 especially in the connective tissue 5 can be achieved with the membrane 6a.

The inner layer 7, outer layer 8, central structure 9 and median structure 12 are at least partially composed of a natural, i.e., endogenous or patient's own material. These structures are created using a suitable tissue engineering technology by propagation and differentiation of a patient's own cell material. Instead of, or in addition to this, the inner layer 7, outer layer 8, central structure 9 and median structure 12 can be composed of at least to a partial extent, a material simulating a natural material, preferably a synthetically simulated material, e.g. collagen and/or hydroxyl-apatite.

The goal of using the membrane 6 or 6a is integration of the tooth implant 1 in a natural structure, corresponding to the natural periodontal structure, formed by the tissue surrounding the tooth implant 1, i.e. the inner layer 7, outer layer 8, central structure 9 and median structure 12 of the membrane 6 or 6a serve primarily to promote this integration. Accordingly, the membrane 6 or 6a preferably is made up of a material which—insofar as it is not the natural or patient's own material—during assimilation or healing of the tooth implant 1, is increasingly resorbed by the natural and/or alveolar or supra-alveolar tissue surrounding and/or forming around the implant. The carrier substrate, if present, likewise consists of resorbing material.

It goes without saying that also in the case of the membrane 6a, the course or the orientation of fibers 10 forming the central structures 9 is selected corresponding to the positioning on the implant corpus 3, as described above for the membrane 6. Further, the membranes 6 and 6a can be designed so that they extend over at least two or also all areas I-IV of the tooth implant 1 and that the fibers 10 of the central structures 9 then have the corresponding orientation.

Figure 8:
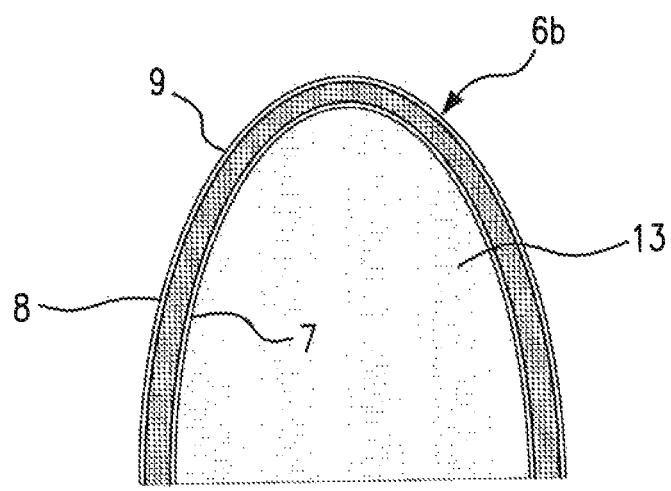
FIG. 8 shows a simplified representation of an alveolar ridge in cross section, together with an at least two-dimensional membrane for regeneration and/or apposition of bone tissue.

FIG. 8 shows as a further embodiment a membrane 6b, which differs from the membrane 6 in that it is designed to be used for regeneration of the bone tissue in the area of an alveolar ridge 13. The membrane 6b is made up of the two exterior layers, that is, inner layer 7 and outer layer 8, and of the central structure 9. As with the prior embodiments, the central structure 9 is formed by the fibers 10 and, if applicable, also by the fibers 11 crossing the fibers 10. The fibers 10 are oriented with their longitudinal extension perpendicular or essentially perpendicular to the inner layer 7 and the outer layer 8. Also, in the case of the membrane 6b, the inner layer 7, outer layer 8 and central structure 9 preferably are embodied in the porous or lattice-like carrier substrate.

The membranes 6, 6a and 6b and/or their carrier substrates are equipped with a memory function, in the manner that the volume or the thickness of the membranes, after triggering the memory function, by the introduction of energy or by canceling a function that initially blocks the memory function, increases by extending the central structures 9, in order to ensure that after insertion of the implant corpus 3 provided with at least one membrane 6 and/or 6a into a prepared alveolus, secure contact of the membrane against the surrounding tissue is achieved.

Especially for this memory function, the fibers 10, upon triggering of the memory function in the necessary manner, can be extended elastically or permanently, or the fibers 10 are initially wavy fibers, which upon triggering of the memory function increasingly transform into an extended state.

The membranes 6, 6a, 6b and/or any carrier substrates of these membranes further are designed so that in the use case, a permanent deformation of the respective membrane, by mechanical extension, compression, etc. is possible in order to adapt the shape of the membrane 6, 6a, 6b to the respective required shape in the use case. In this embodiment, the carrier substrate is made up of a lattice structure that is formed by fibers, namely a biologically compatible and preferably resorbable material.

Further, it can be advantageous to design the respective carrier substrate or its substrate corpus and especially the substrate corpus of the resorbable material, so that it is initially cell-occlusive, i.e. not penetrable for natural cells, but permeable for nutrients, oxygen and metabolites. This makes it possible to create different inner layer 7, outer layer 8 and central structure 9 through propagation and differentiation of natural cells.

The invention was described above based on exemplary embodiments. It goes without saying that numerous modifications and variations are possible, without abandoning the underlying inventive idea on which the invention is based.

REFERENCE FIRST 1 tooth implant
2 bone tissue 3 implant corpus
4 Cap
5 connective tissue
6, 6a, 6b Membrane
7 Exterior inner layer
8 Exterior outer layer
9 Central Structure
10, 11 fibers or ligament
12 Median Structure
13 alveolar ridge
A axis of the longitudinal extension of implant corpus 3

What is claimed is:

1. A dental membrane configured to be attached to an outer surface of a dental implant for regeneration and/or inducing of a tissue and for use in direct contact with a bone tissue or a connective tissue, wherein the dental membrane comprises at least one central structure between an inner layer and an outer layer, at least one of the inner layer and the outer layer is provided to a partial extent with endogenous bone cells or desmodontal cells and the at least one central structure comprises a lattice-like three-dimensional carrier structure configured to surround a dental implant, the lattice-like three-dimensional carrier structure having a fibrous inner layer and a fibrous outer layer with a plurality of fibers oriented radially or essentially radially to a central axis (A) of the dental implant when the dental membrane is attached to the outer surface of the dental implant oriented perpendicular or essentially perpendicular to the fibrous inner layer and the fibrous outer layer, such that the plurality of fibers connect the fibrous inner layer and the fibrous outer layer of the lattice-like three-dimensional carrier structure, and wherein the lattice-like three-dimensional carrier structure of the dental membrane has a memory function that enables the dental membrane to extend elastically or permanently surrounding the dental implant, due to the plurality of fibers incorporated therein, enabling the dental membrane to adapt to a shape for each unique end use for achieving a secure contact of the dental implant and dental membrane against the tissue.

2. The dental membrane according to claim 1, wherein the plurality of fibers of the at least one central structure comprise a changing orientation in relation to the inner and the outer layers along an axis direction (A).

3. The dental membrane according to claim 1, further comprising between the inner and the outer layers at least two central structures composed of the plurality of fibers, the at least two central structures being separated by a median structure, the median structure is at least partially composed of endogenous bone cells or desmodontal cells.

4. The dental membrane according to claim 1, wherein the dental membrane is at least partially composed an endogenous material or of a material that simulates collagen or hydroxyl-apatite, or combinations thereof.

* * * * *